United States Patent
Bosch et al.

(10) Patent No.: US 6,656,504 B1
(45) Date of Patent: Dec. 2, 2003

(54) NANOPARTICULATE COMPOSITIONS COMPRISING AMORPHOUS CYCLOSPORINE AND METHODS OF MAKING AND USING SUCH COMPOSITIONS

(75) Inventors: H. William Bosch, Bryn Mawr, PA (US); Kevin D. Ostrander, Reading, PA (US); Douglas C. Hovey, Collegeville, PA (US)

(73) Assignee: Elan Pharma International Ltd., Shannon (IE)

( * ) Notice: Subject to any disclaimer, the term of this patent is extended or adjusted under 35 U.S.C. 154(b) by 0 days.

(21) Appl. No.: 09/392,557

(22) Filed: Sep. 9, 1999

(51) Int. Cl.[7] .............................. A61K 9/14; A61K 9/50; A61K 38/00

(52) U.S. Cl. ....................... 424/489; 424/501; 424/502; 514/11

(58) Field of Search ................... 424/489, 501, 424/502; 514/11, 937

(56) References Cited

U.S. PATENT DOCUMENTS

| | | | |
|---|---|---|---|
| 3,911,099 A | * 10/1975 | DeFoney et al. | |
| 4,540,602 A | 9/1985 | Motoyama et al. | 427/213.31 |
| 4,727,077 A | 2/1988 | Haga et al. | 514/274 |
| 4,783,484 A | 11/1988 | Violante et al. | 514/535 |
| 4,826,689 A | 5/1989 | Violanto et al. | 424/489 |
| 4,851,421 A | 7/1989 | Iwasaki et al. | 514/352 |
| 4,904,668 A | 2/1990 | Kondo et al. | 514/274 |
| 4,983,605 A | 1/1991 | Kondo et al. | 514/247 |
| 4,997,454 A | 3/1991 | Violante et al. | 23/305 A |
| 5,002,952 A | 3/1991 | Kondo et al. | 514/274 |
| 5,098,907 A | 3/1992 | Kondo et al. | 514/274 |
| 5,145,684 A | 9/1992 | Liversidge et al. | 424/489 |
| 5,264,213 A | 11/1993 | Shibahara et al. | 424/409 |
| 5,389,382 A | * 2/1995 | List et al. | |
| 5,399,363 A | 3/1995 | Liversidge et al. | 424/490 |
| 5,429,824 A | 7/1995 | June | 424/489 |
| 5,439,686 A | 8/1995 | Desai | 424/451 |

(List continued on next page.)

FOREIGN PATENT DOCUMENTS

| | | |
|---|---|---|
| EP | 0 262 560 A2 | 9/1987 |
| FR | 2 608 427 | 6/1988 |
| WO | WO 96/14079 | 5/1996 |
| WO | WO 96/31202 | 10/1996 |
| WO | WO 97/35603 | 10/1997 |
| WO | 98/14174 | 4/1998 |

OTHER PUBLICATIONS

Physicians Desk Reference "Neoral Sandimmune", 2000.*
Kondo et al., "Improved Oral Absorption of Enteric Coprecipitates of a Poorly Soluble Drug," *J. Pharm. Sciences*, 83(4):566–570 (1994).
Kondo et al., "Improved Oral Absorption of a Poorly Water–Soluble Drug, HO–221, by Wet–Bead Milling Producing Particles in Submicron Region," *Chem. Pharm. Bull.*, 41(4):737–740 (1993).
Kondo, et al., "Pharmacokinetics of a Micronized, Poorly Water Soluble Drug, HO–221, in Experimental Animals, "*Biol. Pharm. Bull.*, 16(8):796–800 (1993).
The Merck Index: An Encyclopedia of Chemicals, Drugs, and Biologicals (12th Ed. 1996) pp. 464–465.

*Primary Examiner*—Thurman K. Page
*Assistant Examiner*—Amy E Pulliam
(74) *Attorney, Agent, or Firm*—Foley & Lardner (57) ABSTRACT

Nanoparticulate amorphous cyclosporine formulations, and nanoparticulate cyclosporine formulations comprising a mixture of amorphous and crystalline cyclosporine, having effective average particle sizes of less than about 2000 nm are described. The compositions exhibit increased bioavailability and increased consistency of bioavailability as compared to prior macro-sized cyclosporine and formulations. Methods of making and using the compositions are also described.

59 Claims, 3 Drawing Sheets

U.S. PATENT DOCUMENTS

| | | |
|---|---|---|
| 5,494,683 A | 2/1996 | Liversidge et al. .......... 424/490 |
| 5,510,118 A * | 4/1996 | Bosch et al. ................. 424/489 |
| 5,518,187 A | 5/1996 | Bruno et al. ..................... 241/5 |
| 5,565,188 A | 10/1996 | Wong et al. .............. 424/9.411 |
| 5,587,143 A | 12/1996 | Wong ........................... 424/9.1 |
| 5,622,938 A | 4/1997 | Wong ........................... 424/493 |
| 5,718,388 A | 2/1998 | Czekai et al. ................. 241/21 |
| 5,741,522 A | 4/1998 | Violante et al. ............. 424/489 |
| 5,766,629 A * | 6/1998 | Cho et al. .................... 424/455 |
| 5,776,496 A | 7/1998 | Violante et al. ............. 424/489 |
| 5,827,822 A * | 10/1998 | Floc'H et al. ................. 514/11 |
| 5,834,017 A * | 11/1998 | Cho et al. .................... 424/455 |
| 5,862,999 A | 1/1999 | Czekai et al. ................. 241/21 |
| 6,228,399 B1 | 5/2001 | Parikh et al. |

\* cited by examiner

FIG. 1
REPRESENTATIVE X-RAY POWDER DIFFRACTION PATTERN OF CRYSTALLINE CYCLOSPORINE DRUG SUBSTANCE

NANOPARTICULATE COMPOSITIONS COMPRISING AMORPHOUS CYCLOSPORINE AND METHODS OF MAKING AND USING SUCH COMPOSITIONS

FIELD OF THE INVENTION

The present invention is directed to nanoparticulate compositions comprising amorphous cyclosporine, or a mixture of amorphous and crystalline cyclosporine, and methods of making and using such compositions.

BACKGROUND OF THE INVENTION

Cyclosporine is a hydrophobic, cyclic, undecapeptide that exerts immunosuppressive, antiinflammatory, antifungal, and antiparasitic activities. Immunosuppressive medications play a large part of the management of many pediatric illnesses. Cyclosporine is the primary tool used to prevent rejection following solid organ and bone marrow transplantation; the drug helped revolutionize transplantation by improving transplant survival, reducing hospitalization, and reducing patient morbidity. It has been estimated that cyclosporine is given to more than 90% of children who have received a kidney transplant in the United States. Cyclosporine also has been effective in various other autoimmune conditions such as uveitis, psoriasis, type I diabetes mellitus, rheumatoid arthritis, inflammatory bowel disease, certain nephropathies, refractory Crohn's disease, ulcerative colitis, biliary cirrhosis, aplastic anemia, rheumatoid arthritis, myasthenia gravis, and dermatomyositis.

Cyclosporine is in clinical use worldwide under the trade names SANDIMMUNE® (Novartis), NEORAL® (Novartis), and SANGCYA® (SangStat). SANDIMMUNE®, introduced in 1983, suffered from poor and widely variable absorption rates. This prompted development of a second generation cyclosporine formulation, NEORAL®, which is a microemulsion formulation having better absorption than SANDIMUNE®-both in quantity and consistency. Since 1995, when NEORAL® was introduced, about 70% of patients have switched from SANDIMMUNE® to NEORAL®, indicating the severity of poor and inconsistent absorption of cyclosporine. SANGCYA®, which is a modified oral solution bioequivalent to NEORAL®, was introduced in 1998.

Cyclosporine is administered orally and intravenously (IV). After oral administration, roughly 20 to 50% is absorbed, although absorption is highly variable. First-pass metabolism, mode of administration, and drug interactions all affect cyclosporine absorption. Food decreases the absorption of NEORAL® and SANGCYA®.

Cyclosporine is extremely hydrophobic. The IV formulation contains 33% alcohol and a castor oil vehicle to solubilize the drug, which is believed to account for occasionally severe hypersensitivity reactions. Oral preparations can contain corn, castor or olive oil and ethanol, but in lower concentrations. The dose normalized area under the curve (AUC) is 23% greater for NEORAL® or SANGCYA® as compared to SANDIMUNE® in renal transplant, rheumatoid arthritis, and psoriasis patients, and 50% greater in liver transplant patients. Data for cardiac transplant patients is limited, but similar increases have been noted. Increases in peak blood cyclosporine concentrations (NEORAL® and SANGCYA® related to SANDIMMUNE®) range from 40 to 106% for renal transplant patients and 90% for liver transplant patients.

While NEORAL® and SANGCYA® are an improvement over SANDIMMUNE®, the conventional cyclosporine formulations suffer from poor bioavailability because, among other things, cyclosporine is poorly water soluble. Moreover, currently marketed cyclosporine formulations are known to have disadvantageous "intersubject variability," i.e., it has been found that, given the same dosage amount, actual blood levels of cyclosporine vary significantly from patient to patient. See *Physicians' Desk Reference* (1998) at 1882 et seq. This represents an important shortcoming of these drugs. Specifically, because cyclosporine has a narrow therapeutic index (a narrow range between an effective dosage and a harmful dosage), the inability to predict drug absorption requires that physicians closely monitor each patient to establish baseline absorption levels. Such monitoring is expensive and time consuming. In addition, the poor absorption and patient variability of known cyclosporine formulations can make dosage formulation difficult. Proper dosage formulation for cyclosporine is critical because the drug is a general immunosuppressive. Therefore, the drug can result in an increased susceptibility to infection. Too much drug can result in uncontrolled infection while too little can result in organ rejection.

One drug delivery method that can result in increasing the bioavailability, increasing the absorption rate, quantity, and consistency, and decreasing the toxicity of a drug is formulation of the drug into a nanoparticulate composition. Nanoparticulate compositions, first described in U.S. Pat. No. 5,145,684 ("the '684 patent"), are particles consisting of a poorly soluble crystalline therapeutic or diagnostic agent onto which are adsorbed a non-crosslinked surface stabilizer. Nanoparticulate compositions comprising cyclosporine are not described by the '684 patent. Nanoparticulate compositions containing crystalline, but not amorphous, cyclosporine are disclosed in U.S. Pat. Nos. 5,494,683 and 5,399,363.

Conventional large particle sized amorphous cyclosporine compositions are described in U.S. Pat. Nos. 5,389,382 ("the '382 patent") and 5,827,822 ("the '822 patent"). These disclosures suffer from various deficiencies. For example, the '382 patent describes hydrosols of cyclosporine in an intravenous applicable, stabilized, pharmaceutically acceptable form, which is suspended or dry. The hydrosol formulations are obtained by controlled precipitation methods. Such methods are disadvantageous in that they result in solid dose formulations having a low drug to surface stabilizer ratio, and liquid dispersion formulations having a low solid content. This is because controlled precipitation methods require an excess amount of surface stabilizer and water to produce small-sized precipitated particles. The excess of surface stabilizer produces solid dose compositions having a large quantity of surface stabilizer and a small quantity of drug, and the excess of water produces a liquid dispersion formulation having a low solids content and, therefore, a low drug content.

A high drug content for a solid dose or liquid dispersion formulation is preferred because it produces a more concentrated dosage formulation. Concentrated dosage forms of cyclosporine are particularly desirable because the dosage for this drug is relatively high, i.e., about 100 mg a day or more. A dosage formulation having a low drug content, but requiring a high daily dosage, results in either a large pill, capsule, or quantity of fluid, or multiple doses of such formulations, to be administered to the patient. In contrast, a concentrated dosage form allows minimization of the size of the orally administered pill or capsule or number of daily administrations.

The '822 patent is directed to aqueous suspension formulations of amorphous cyclosporin A containing lower alkanols as solubilizing agents and a polyoxyalkylene surfactant. The addition of alcohol solubilizing agents is frequently undesirable because they can an trigger an allergic response in a patient. Such solubilizing agents are often required for prior art cyclosporine compositions to increase the solubility of the cyclosporine. A drug must be absorbed by a patient prior to taking effect. Thus, often pharmaceutical formulations of highly insoluble drugs additionally contain solubilizing agents to aid in absorption of the drug following administration.

There remains a need in the art for cyclosporine formulations that can be delivered in high dosage formulations, that exhibit consistent and effective absorption, that have decreased toxicity as compared to known cyclosporine formulations, and which do not require the presence of alcohol solubilizing agents. The present invention satisfies these needs.

SUMMARY OF THE INVENTION

The present invention is directed to nanoparticulate compositions of amorphous cyclosporine and, adsorbed to the surface of the cyclosporine, at least one non-crosslinked surface stabilizer. The cyclosporine particles of the nanoparticulate composition have an effective average particle size of less than about 2000 nm.

In another embodiment, the invention encompasses nanoparticulate compositions of a mixture of amorphous and crystalline cyclosporine and, adsorbed to the surface of the cyclosporine, at least one non-crosslinked surface stabilizer. The cyclosporine particles of the nanoparticulate composition have an effective average particle size of less than about 2000 nm.

Another aspect of the invention is directed to pharmaceutical compositions comprising one or more nanoparticulate compositions of the invention. The pharmaceutical composition preferably comprises a nanoparticulate composition described above and a pharmaceutically acceptable carrier, as well as any desired excipients. The compositions, which can be delivered in high dosage formulations, provide for improved consistency of cyclosporine absorption from patient to patient for a given dosage amount, exhibit decreased toxicity, and exhibit increased absorption as compared to conventional cyclosporine formulations.

This invention further discloses methods of making nanoparticulate compositions according to the invention. A first method comprises contacting amorphous cyclosporine, or a mixture of amorphous and crystalline cyclosporine, with at least one surface stabilizer for a time and under conditions sufficient to provide a stable nanoparticulate composition. The surface stabilizer can be contacted with the cyclosporine particles either before, during, or after size reduction of the cyclosporine particles. The cyclosporine particles of the nanoparticulate composition have an effective average particle size of less than about 2000 nm.

The present invention is further directed to methods of treatment comprising administering to a mammal in need a therapeutically effective amount of a nanoparticulate composition according to the invention. The nanoparticulate cyclosporine composition can be administered via any conventional route.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

The present invention is directed to compositions comprising nanoparticulate amorphous cyclosporine, or a mixture of amorphous and crystalline cyclosporine, and methods of making and using such nanoparticulate compositions. As used herein, singular terms are used for simplicity of expression only and are not intended to limit the invention or aspects of the invention to singular embodiments. Thus, the description of, for example, "a surface stabilizer" is meant to describe "one or more" surface stabilizers unless explicitly indicated otherwise.

Prior to the present invention, it was known that crystalline drugs could be formulated into nanoparticulate compositions, as taught by the '684 patent. In such compositions, a surface stabilizer adsorbs to the crystalline surface of the drug and acts as a steric barrier to other drug particles to prevent agglomeration. This results in a stable nanoparticulate composition, in which the particle size of the composition does not significantly increase over time via solubilization and recrystallization or agglomeration. Because the surface stabilizer adsorbs to the surface of the crystalline drug, and does not chemically interact with the drug, it was thought that amorphous drugs could not be utilized in nanoparticulate compositions described by the '684 patent. Amorphous drugs do not have an intermolecular lattice structure, which is characteristic of the crystalline solid state. Surprisingly, it was discovered that amorphous cyclosporine can be incorporated into a nanoparticulate composition.

An amorphous compound has a higher energy level than a crystalline compound. Because of this, an amorphous compound is generally unstable, as in nature the compound prefers to convert to the lower energy crystalline state. Because amorphous compounds have a higher energy level than crystalline compounds, it is preferable that a drug be in an amorphous state. The amorphous state is less stable than the crystalline state; therefore, a solid will be more soluble in the amorphous state than in the crystalline state. Improved solubility will lead to rapid and more complete dissolution, and in the case of a poorly soluble drug substance, improved bioavailability.

A. Compositions

The compositions of the invention comprise nanoparticulate amorphous cyclosporine, or a mixture of amorphous and crystalline cyclosporine, having one or more surface stabilizers adsorbed to the surface of the cyclosporine. Surface stabilizers useful herein physically adhere to the surface of the nanoparticulate cyclosporine but do not chemically react with the cyclosporine itself. Individually adsorbed molecules of the surface stabilizer are essentially free of intermolecular crosslinkages.

The present invention also includes nanoparticulate compositions formulated into compositions together with one or more non-toxic physiologically acceptable carriers, adjuvants, or vehicles, collectively referred to as carriers, for parenteral injection, for oral administration, for rectal or topical administration, or the like. The present invention further includes nanoparticulate compositions in solid dose formulations and liquid dispersion formulations.

1. Cyclosporine

The cyclosporins comprise a class of cyclic non-polar oligopeptides having valuable immunosuppressive, anti-inflammatory, and anti-parasitic activity. The first of the cyclosporins to be isolated and what has been termed the "parent" compound of the class is the naturally occurring fungal metabolite referred to simply as "cyclosporine" or as "cyclosporin A."

Since the discovery of cyclosporin A, a wide variety of naturally occurring cyclosporins have been isolated and identified and other non-naturally occurring cyclosporins have been prepared by synthetic means or via modified culture techniques. Such compounds are known in the art and are described, for example, in U.S. Pat. No. 5,389,382 and in *The Merck Index* (12$^{th}$ ed. 1996) at 464–465. As used herein, the term cyclosporine is meant to include both cyclosporin A and other cyclosporins, such as cyclosporins B through I and synthetic analogues thereof. The preferred cyclosporin used herein is cyclosporin A.

The cyclosporine compositions of the present invention are either partially or predominantly amorphous in nature. This is so even though the starting cyclosporine compound used to obtain the nanoparticulate compositions may be predominantly crystalline in nature. The term "amorphous" is a term with a recognized meaning in the chemical arts and describes a structure that is non-crystalline, i.e., a structure that lacks an intermolecular lattice structure. Whether the nanoparticulate composition is in a crystalline or amorphous state can be determined, for example, by X-ray powder diffraction patterns or other methods known to the skilled artisan.

2. Surface Stabilizers

Suitable surface stabilizers can preferably be selected from known organic and inorganic pharmaceutical excipients. Such excipients include various polymers, low molecular weight oligomers, natural products, and surfactants. Preferred surface stabilizers include nonionic and ionic surfactants. Two or more surface stabilizers can be used in combination.

Representative examples of surface stabilizers include cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Specialty Chemicals)); polyethylene glycols (e.g., Carbowaxs 3350® and 1450®, and Carbopol 934® (Union Carbide)), dodecyl trimethyl ammonium bromide, polyoxyethylene stearates, colloidal silicon dioxide, phosphates, sodium dodecylsulfate, carboxymethylcellulose calcium, hydroxypropyl celluloses (e.g., HPC, HPC-SL, and HPC-L), hydroxypropyl methylcellulose (HPMC), carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)); a charged phospholipid such as dimyristoyl phophatidyl glycerol, dioctylsulfosuccinate (DOSS); Tetronic 1508® (T-1508) (BASF Corporation), dialkylesters of sodium sulfosuccinic acid (e.g., Aerosol OT®, which is a dioctyl ester of sodium sulfosuccinic acid (American Cyanamid)); Duponol P®, which is a sodium lauryl sulfate (DuPont); Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-10G® or Surfactant 10-G® (Olin Chemicals, Stamford, Conn.); Crodestas SL-40® (Croda, Inc.); and SA9OHCO, which is $C_{18}H_{37}CH_2(CON(CH_3)-CH_2(CHOH)_4(CH_2OH)_2$ (Eastman Kodak Co.), triblock copolymers of the structure -(-PEO-)--(-PBO-)--(-PEO-)- (known as B20–5000), and the like.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 1986), specifically incorporated by reference. The surface stabilizers are commercially available and/or can be prepared by techniques known in the art.

The invention includes that each of the above-described stabilizers or other stabilizers described herein or described in a reference cited herein can be used either alone, in combination with each other, or with other surface stabilizers.

3. Nanoparticulate Particle Size

Preferably, the compositions of the invention contain nanoparticles which have an effective average particle size of less than about 2000 nm, less than about 1500 nm, less than about 1000 nm, less than about 800 nm, less than about 700 nm, less than about 600 nm, less than about 500 nm, less than about 400 nm, less than about 300 nm, less than about 200 nm, less than about 100 nm, or less than about 50 nm, as measured by light-scattering methods or other methods accepted in the art. By "an effective average particle size of less than about 2000 nm" it is meant that at least 50% of the drug particles have a weight average particle size of less than about 2000 nm when measured by light scattering or other conventional techniques. Preferably, at least 70% of the drug particles have an average particle size of less than about 2000 nm, more preferably at least 90% of the drug particles have an average particle size of less than about 2000 nm, and even more preferably at least about 95% of the particles have a weight average particle size of less than about 2000 nm.

4. Concentration of Cyclosporine and Surface Stabilizer

Preferable ratios of cyclosporine to surface stabilizer are about 10:1 to about 1.5:1, by weight. With liquid dispersions, preferred drug content is about 50% to about 2% by weight.

B. Methods of Making Nanoparticulate Formulations

Exemplary methods of making nanoparticulate compositions are described in the '684 patent. The optimal effective average particle size of the invention can be obtained by controlling the process of particle size reduction, such as by controlling the milling time and the amount of surface stabilizer added. Particle growth and particle aggregation can also be minimized by milling the composition under colder temperatures and by storing the final composition at colder temperatures.

Milling to obtain a nanoparticulate composition comprises dispersing cyclosporine particles in a liquid dispersion medium, followed by applying mechanical means in the presence of grinding media to reduce the particle size of the cyclosporine to the desired effective average particle size. The cyclosporine particles can be reduced in size in the presence of one or more surface stabilizers. Alternatively, the cyclosporine particles can be contacted with one or more surface stabilizers after attrition. Other compounds, such as a diluent, can be added to the cyclosporine/surface stabilizer composition during the size reduction process. Dispersions can be manufactured continuously or in a batch mode. The resultant nanoparticulate cyclosporine dispersion can be utilized in solid or liquid dosage formulations. Exemplary useful mills include low energy mills, such as a roller or ball mill, and high energy mills, such as Dyno mills, Netzsch mills, DC mills, and Planetary mills.

The starting cyclosporine composition can be predominantly crystalline, predominantly amorphous, or a mixture thereof. The resultant cyclosporine composition is predominantly amorphous.

A solid dosage formulation can be prepared by drying the nanoparticulate amorphous cyclosporine, or mixture of amorphous and crystalline cyclosporine, following grinding. A preferred drying method is spray drying. The spray drying process is used to obtain a nanoparticulate powder following the milling process used to transform the cyclosporine into nanoparticles. Such a nanoparticulate powder can be formulated into tablets for oral administration.

C. Methods of Using Nanoparticulate Compositions of the Invention

The nanoparticulate compositions of the invention can be administered to humans and animals either orally, rectally, parenterally (intravenous, intramuscular, or subcutaneous), intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents, or vehicles including water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

The nanoparticulate compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include capsules, tablets, pills, powders, and granules. In such solid dosage forms, the active compound is admixed with at least one of the following: (a) one or more inert excipients (or carrier), such as dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active compounds, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Actual dosage levels of active ingredients in the nanoparticulate compositions of the invention may be varied to obtain an amount of active ingredient that is effective to obtain a desired therapeutic response for a particular composition and method of administration. The selected dosage level therefore depends upon the desired therapeutic effect, on the route of administration, on the desired duration of treatment, and other factors.

The total daily dose of the compounds of this invention administered to a host in single or divided dose can vary widely depending upon a variety of factors, including the body weight, general health, sex, diet, time and route of administration, rates of absorption and excretion, combination with other drugs, and the severity of the particular condition being treated. For example, the recommended daily dosage for NEORAL® ranges from 9±3 mg/kg/day for renal transplant patients to 2.5 mg/kg/day for psoriasis and rheumatoid arthritis, while the suggested initial oral dosage of SANDIMMUNE® for transplant patients is 10–18 mg/kg/day.

The following examples are given to illustrate the present invention. It should be understood, however, that the invention is not to be limited to the specific conditions or details described in these examples. Throughout the specification, any and all references to a publicly available document, including U.S. patents, are specifically incorporated into this patent application by reference.

EXAMPLE 1

The purpose of this example was to prepare nanoparticulate cyclosporine formulations in which the cyclosporine is predominantly amorphous.

The nanoparticulate amorphous cyclosporine formulations described in Table 1 were obtained using high energy media milling techniques. All milling experiments utilized a DYNO-MILL® Type KDL (Willy Bachofen AG, Basel, Switzerland) assembled with a 0.15 L chamber. Cyclosporine was manufactured by the North China Pharmaceutical Corporation (Shijiazhuang, China). Particle size distributions were determined using a Horiba LA-910 light-scattering particle size analyzer (Horiba Instruments, Irvine, Calif.).

(1) 10% Cyclosporine, 6% F108, 0.1% SLS

The nanoparticulate composition (1) was prepared by dissolving 5.1 g of Pluronic® F108 and 0.085 g of sodium lauryl sulfate (SLS) in 71.32 g of deionized water. The stabilizer solution, along with 8.5 g of cyclosporine drug substance and 500 μm polymeric attrition media were charged into the milling chamber. The formulation was processed for 6 hours, then harvested and filtered. The final particle size distribution was mean=275 nm, 90%<420 nm.

(2) 5% Cyclosporine, 1.5% HPC-SL, 0.15% SLS

The nanoparticulate composition (2) was prepared by dissolving 1.28 g of HPC-SL (Nippon Soda) and 0.085 g of sodium lauryl sulfate (SLS) in 79.38 g of deionized water. The stabilizer solution, along with 4.25 g of cyclosporine drug substance and 500 μm polymeric attrition media were charged into the milling chamber. The formulation was processed for 4 hours. The concentration of SLS was then increased to 0.15%. The dispersion was milled for an additional 0.5 hour and then isolated from the attrition media by filtration. The final particle size distribution was mean=268 nm, 90% <380nm.

(3) 5% Cyclosporine, 1% Tyloxapol

The nanoparticulate composition (3) was prepared by dissolving 0.85 g of tyloxapol (Nycomed) in 79.9 g of deionized water. The stabilizer solution, along with 4.25 g of cyclosporine drug substance and 500 μm polymeric attrition media were charged into the milling chamber. The formulation was processed for 3 hours and then isolated from the attrition media by filtration. The final particle size distribution was mean=213 nm, 90%<304 nm.

(4) 5% Cyclosporine, 2% B20–5000

The nanoparticulate composition (4) was prepared by dissolving 0.85 g of B20–5000 (Dow Chemical) in 79.9 g of deionized water. The stabilizer solution, along with 4.25 g of cyclosporine drug substance and 500 μm polymeric attrition media were charged into the milling chamber. The formulation was processed for 4.5 hours. At that time, an additional 0.85 g of B20–5000 was added. The dispersion was milled for an additional 2.25 hours and then isolated from the attrition media by filtration. The final particle size distribution was mean=292 nm, 90%<411 nm.

(5) 5% Cyclosporine, 2% F108, 1% Tyloxapol

The nanoparticulate composition (5) was prepared by dissolving 1.7 g of Pluronic® F108 (BASF) and 0.85 g of tyloxapol (Nycomed) in 78.2 g of deionized water. The stabilizer solution, along with 4.25 g of cyclosporine drug substance and 500 μm polymeric attrition media were charged into the milling chamber. The formulation was processed for 7 hours and then isolated from the attrition media by filtration. The final particle size distribution was mean=192 nm, 90%<300 nm by Horiba LA-910.

(6) 5% Cyclosporine, 0.5% SLS

The nanoparticulate composition (6) was prepared by dissolving 0.425 g of sodium lauryl sulfate (Spectrum) in 80.33 g of deionized water. The stabilizer solution, along with 4.25 g of cyclosporine drug substance and 500 μm polymeric attrition media were charged into the milling chamber. The formulation was processed for 3 hours and then isolated from the attrition media by filtration. The final particle size distribution was mean=182 nm, 90%<265 nm.

Figure 1:
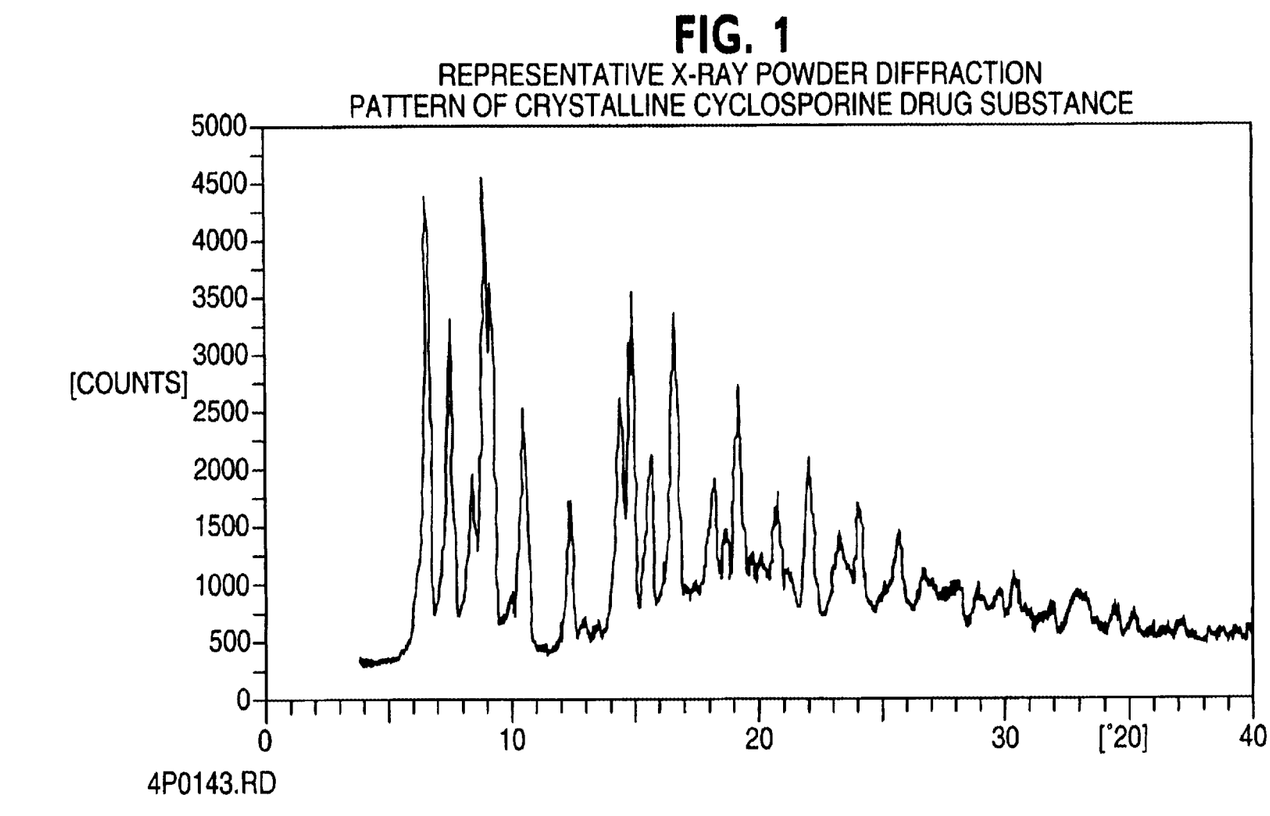
FIG. 1: Shows the results of x-ray powder diffraction of raw cyclosporine drug substance.
Figure 2:
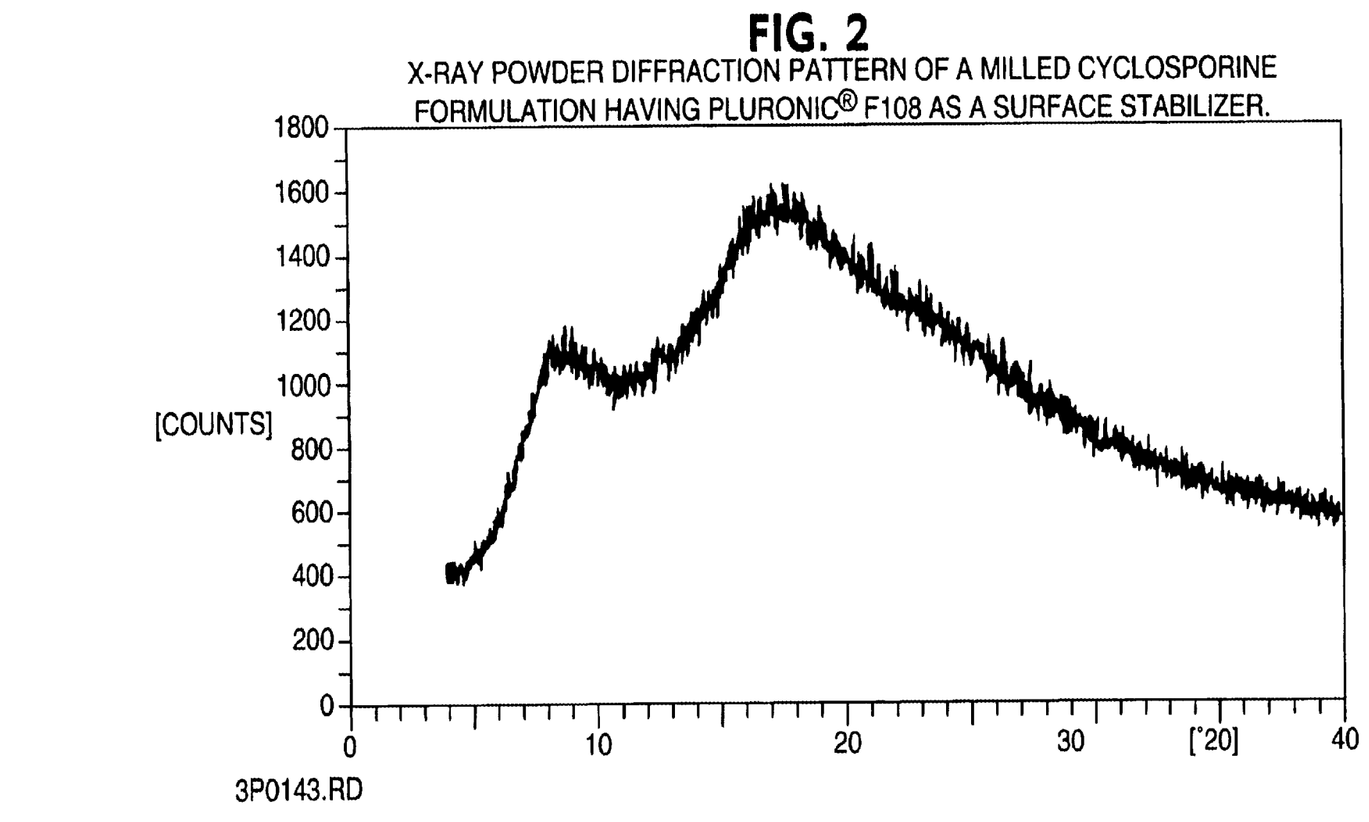
FIG. 2: Shows the results of x-ray powder diffraction of a milled cyclosporine formulation having Pluronic® F108 as a surface stabilizer.
Figure 3:
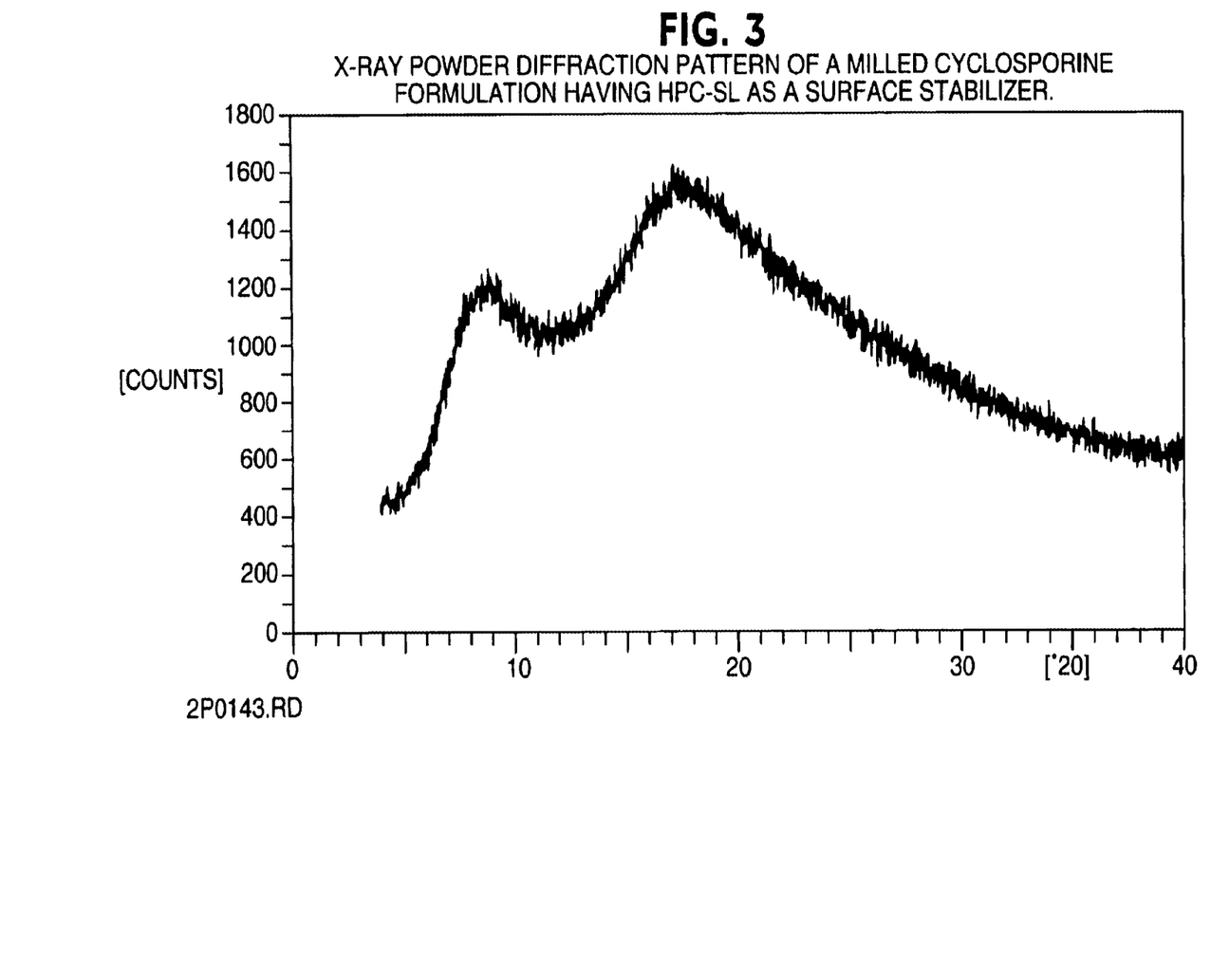
FIG. 3: Shows the results of x-ray powder diffraction of a milled cyclosporine formulation having HPC-SL as a surface stabilizer.

The drug substance starting material used in these examples was primarily crystalline as determined by x-ray powder diffraction, the results of which are shown in FIG. 1. After two representative experiments the milled colloidal dispersions were also analyzed by x-ray powder diffraction. Upon completion of milling, a portion of each dispersion was centrifuged and the supernatant liquid decanted. The solids were washed with water and re-centrifuged several times, then dried. X-ray powder diffraction of the milled material showed the absence of sharp absorption lines, indicating that the material was amorphous, as shown in FIGS. 2 and 3. FIG. 2 shows the results of x-ray powder diffraction of milled cyclosporine having Pluronic® F108 as a surface stabilizer, and FIG. 3 shows the results of x-ray powder diffraction of milled cyclosporine having HPC-SL as a surface stabilizer. The colloidal dispersions could also be prepared from amorphous drug substance starting material.

TABLE 1

Nanoparticulate Amorphous Cyclosporine Formulations

| Formulation | Particle Size |
| --- | --- |
| (1) 10% cyclosporine, 6% Pluronic ® F108, and 0.1% sodium lauryl sulfate (SLS) | Mean = 275 nm<br>90% less than 420 nm |
| (2) 5% cyclosporine, 1.5% HPC-SL, 0.1% SLS | Mean = 268 nm<br>90% less than 380 nm |
| (3) 5% cyclosporine, 1% tyloxapol | Mean = 213 nm<br>90% less than 304 nm |
| (4) 5% cyclosporine, 2% B20-5000 | Mean = 292 nm<br>90% less than 411 nm |
| (5) 5% cyclosporine, 2% Pluronic ® F108, 1% tyloxapol | Mean = 192 nm<br>90% less than 300 nm |
| (6) 5% cyclosporine, 0.5% SLS | Mean = 182 nm<br>90% less than 265 nm |

The results show that a nanoparticulate amorphous cyclosporine formulation can be made using a variety of surface stabilizers, using various stabilizer concentrations, and using various cyclosporine concentrations, from crystalline cyclosporine starting material.

EXAMPLE 2

The purpose of this example was to compare the pharmacokinetic profiles between a nanoparticulate cyclosporine formulation according to the invention and a conventional cyclosporine formulation, NEORAL®. The cyclosporine present in NEORAL® is solubilized in alcohol and several additional excipients.

A comparative study was performed between a nanoparticulate amorphous cyclosporin A composition and NEORAL®. The nanoparticulate composition consisted of 10% w/w cyclosporine, 6% w/w Pluronic® F1 08, and 0.1% w/w sodium lauryl sulfate (SLS). The composition was prepared by dissolving 90 g of Pluronic FP108 and 1.5 g of SLS in 1258.5 g of sterile water for injection, USP and then adding 150 g of cyclosporine to form a premix. A DYNO-MILL® Type KDL was assembled with a 600 cc recirculation chamber which was charged with 500 μm polymeric attrition media. The slurry was processed for 12.5 hours and then filtered through a 20 μm capsule filter to yield a nanoparticulate colloidal dispersion of cyclosporine with a mean particle size of 165 nm and 90% less than 229 nm. The particle size distribution was determined on a Horiba LA-910 particle size analyzer.

Tables 2 and 3 show a summary of the Area Under the Curve (AUC) for a single 100 mg dosage of the nanoparticulate amorphous cyclosporin A composition and NEORAL®, respectively, administered to two groups of three dogs (GROUPS 1 and 2) over a 24 hour period. A greater AUC corresponds to greater bioavailability.

periodic increments throughout Day 8 for the GROUP 2 dogs, as shown in Table 2. In addition, the AUC values for NEORAL® administration were measured at periodic increments throughout Day 1 for the GROUP 2 dogs and at periodic increments throughout Day 8 for the GROUP 1 dogs, as shown in Table 3.

TABLE 2

AUC Values for Nanoparticulate Amorphous Cyclosporine

| Time (hrs) | GROUP 1 (Nanoparticulate Amorphous Cyclosporine AUC (ng/mL/hr) for Day 1) | | | GROUP 2 (Nanoparticulate Amorphous Cyclosporine AUC (ng/mL/hr) for Day 8) | | | Average Nanoparticulate Amorphous Cyclosporine |
|---|---|---|---|---|---|---|---|
| | Dog No. 422/m/1 | Dog No. 464/m/1 | Dog No. 408/f/1 | Dog No. 459/m/2 | Dog No. 471/f/2 | Dog No. 472/f/2 | |
| 0.00 | 0.00 | 0.00 | 0.00 | 0.00 | 0.0 | 0.00 | 0.00 |
| 0.25 | 517.37 | 623.23 | 402.13 | 593.58 | 454.7 | 405.27 | 499.37 |
| 0.50 | 1245.78 | 988.99 | 489.15 | 847.55 | 651.9 | 842.43 | 844.30 |
| 1.00 | 1109.14 | 1301.33 | 936.85 | 1112.88 | 830.6 | 1722.52 | 1168.88 |
| 1.50 | 867.24 | 913.68 | 785.06 | 1034.71 | 520.1 | 1456.75 | 929.60 |
| 2.00 | 799.95 | 764.94 | 369.95 | 744.93 | 474.4 | 700.33 | 642.43 |
| 3.00 | 590.29 | 519.93 | 484.13 | 537.58 | 297.9 | 499.84 | 488.28 |
| 4.00 | 344.29 | 327.43 | 331.71 | 352.46 | 202.5 | 603.55 | 360.32 |
| 5.00 | 293.91 | 238.02 | 298.99 | 255.72 | 158.9 | 510.80 | 292.72 |
| 6.00 | 190.82 | 159.78 | 242.17 | 196.16 | 108.4 | 299.89 | 199.54 |
| 8.00 | 132.17 | 121.90 | 120.64 | 50.33 | 78.0 | 150.11 | 108.86 |
| 12.00 | 63.96 | 47.17 | 88.16 | 36.76 | 32.7 | 101.69 | 61.74 |
| 16.00 | 28.59 | 25.15 | 39.89 | 12.33 | 7.7 | 34.55 | 24.71 |
| 24.00 | 0.00 | 5.42 | 2.53 | 0.00 | 0.0 | 11.89 | 3.31 |
| AUC (ng/mL/hr) | 4964.2 | 4593.2 | 4473.3 | 4155.9 | 2833.8 | 6387.3 | 4567.0* |

*Standard Deviation = 1154; Relative Standard Deviation = 25.3

TABLE 3

AUC Values for NEORAL®

| Time (hrs) | GROUP 2 (NEORAL® AUC (ng/mL/hr) Day 1) | | | GROUP 1 (NEORAL® AUC (ng/mL/hr) Day 8) | | | Average NEORAL® |
|---|---|---|---|---|---|---|---|
| | Dog No. 459/m/2 | Dog No. 471/f/2 | Dog No. 472/f/2 | Dog No. 422/m/1 | Dog No. 464/m/1 | Dog No. 408/f/1 | |
| 0.00 | 0.00 | 0.0 | 0.00 | 0.00 | 0.00 | 0.00 | 0.00 |
| 0.25 | 66.50 | 164.2 | 393.04 | 373.74 | 106.16 | 0.00 | 183.93 |
| 0.50 | 514.48 | 484.0 | 747.36 | 1037.03 | 572.61 | 0.00 | 559.25 |
| 1.00 | 1025.13 | 1077.3 | 1669.62 | 1410.78 | 666.83 | 551.19 | 1066.80 |
| 1.50 | 1384.60 | 1381.5 | 1743.53 | 1454.44 | 872.08 | 1095.92 | 1322.01 |
| 2.00 | 1257.50 | 1315.4 | 1470.21 | 1083.48 | 550.85 | 1242.06 | 1153.25 |
| 3.00 | 897.22 | 742.9 | 1019.74 | 266.04 | 397.52 | 1019.47 | 723.81 |
| 4.00 | 504.60 | 590.3 | 672.18 | 398.97 | 363.83 | 586.29 | 519.37 |
| 5.00 | 377.09 | 476.6 | 560.69 | 296.72 | 197.78 | 118.35 | 337.87 |
| 6.00 | 271.80 | 389.2 | 405.96 | 257.10 | 173.56 | 289.07 | 297.79 |
| 8.00 | 113.10 | 282.9 | 262.83 | 325.91 | 99.31 | 44.87 | 188.15 |
| 12.00 | 105.13 | 189.5 | 412.59 | 66.76 | 14.24 | 100.51 | 148.12 |
| 16.00 | 51.37 | 131.1 | 172.27 | 64.77 | 33.96 | 3.20 | 76.11 |
| 24.00 | 27.85 | 89.7 | 64.67 | 17.14 | 0.00 | 24.76 | 37.35 |
| TOTAL AUC (ng/mL/hr) | 6457.2 | 8982.8 | 12600.6 | 6307.0 | 3355.3 | 5177.1 | 7146.7* |

*Standard Deviation = 3241.9; Relative Standard Deviation = 45.4

To minimize any differences in AUC values observed due to different absorption rates of individual animals, AUC measurements for the nanoparticulate amorphous cyclosporin A composition and NEORAL® were measured following administration to the same animals eight days apart. Thus, the AUC values for the nanoparticulate amorphous cyclosporin A composition were measured at periodic increments throughout Day 1 for the GROUP 1 dogs and at The results show that for the GROUP 1 dogs absorption of the nanoparticulate amorphous cyclosporin A was dramatically consistent, with AUC values of 4964.2, 4593.2, and 4473.3. In contrast, absorption of NEORAL® for the same group of dogs, GROUP 1, was widely variable, with AUC values of 6307.0, 3355.3, and 5177.1 ng/mL/hr. The results for the GROUP 2 dogs were similar, with relatively consistent AUC values for the nanoparticulate amorphous cyclosporin A of 4155.9, 2833.8, and 6387.9 ng/mL/hr. In contrast, the AUC values for the GROUP 2 dogs for NEORAL® administration were 6457.2, 8982.8, and 12600.6 ng/mL/hr. A wide variation in absorption is highly undesirable because it makes dosage formulation difficult and because it can result in requiring constant monitoring of the patient to ensure proper blood levels of the drug. The relative standard deviation (RSD) of the AUC values for each dosage form is a quantitative measure of intersubject absorption variability. Among the dogs receiving nanoparticulate cyclosporine the RSD of the AUC values was 25.4%, whereas the RSD of the AUC values when NEORAL® was adminstered was 45.4%. Thus, the intersubject variability was ca. 1.8 times greater for the NEORAL® dosage form than it was for the nanoparticulate formulation.

TABLE 4

Consistency of Absorption of the Nanoparticulate Amorphous Cyclosporine Formulation and NEORAL ®

| Animals Studied | Nanoparticulate Amorphous Cyclosporine Formulation Total AUC (ng/mL/hr) | NEORAL ® Total AUC (ng/mL/hr) |
|---|---|---|
| GROUP 1 Dogs | | |
| Dog No. 422/m/1 | 4964.2 | 6307.0 |
| Dog No. 464/m/1 | 4593.2 | 3355.3 |
| Dog No. 408/f/1 | 4473.3 | 5177.1 |
| GROUP 2 Dogs | | |
| Dog No. 459/m/2 | 4155.9 | 6457.2 |
| Dog No. 471/f/2 | 2833.8 | 8982.8 |
| Dog No. 472/f/2 | 6387.3 | 12600.6 |
| Relative Standard Deviation | 25.4% | 45.4% |

The variability in absorption for NEORAL® as compared to the nanoparticulate amorphous cyclosporine formulation is also shown by a comparison of the absorption range for each formulation for the same single 100 mg dosage, as shown in Table 5 below. NEORAL® has an intersubject absorption variability in AUC that spans 9245 ng/mL/hr, while the nanoparticulate AUC variability (lowest to highest) is only 3554 ng/mL/hr. Variability in absorption can lead to sub-therapeutic plasma concentrations of drug or, conversely, excessively high plasma concentrations at which the drug substance exerts toxic effects. Such variability is highly undesirable, particularly for a drug such as cyclosporine which has a narrow effective dosage range.

TABLE 5

AUC Variability of NEORAL ® as Compared to the Nanoparticulate Amorphous Cyclosporine Formulation

| Formulation | Highest AUC | Lowest AUC | Difference ng/mL/hr |
|---|---|---|---|
| NEORAL ® | 12600.6 ng/mL/hr | 3355.3 ng/mL/hr | 9245.3 |
| Nanoparticulate Formulation | 6387.3 ng/mL/hr | 2833.8 ng/mL/hr | 3553.5 |

Furthermore, the inconsistency in absorption between NEORAL® and the nanoparticulate amorphous cyclosporine formulation is evidenced by the dramatic differences in absorption in the first 0.50 hour post-dosing. Among the dogs receiving nanoparticulate cyclosporine, all six subjects had detectable plasma concentrations (ranging from 405.27 to 623.23 ng/mL/hr) at 15 minutes post-dosing (Table 2).

When given NEORAL®, five of the six subjects had detectable plasma concentrations (ranging from 66.50 to 393.04 ng/mL/hr) at 15 minutes post-dosing, but one dog (No. 408/f/1) had no detectable blood levels even thirty minutes after receiving the drug (Table 3).

The results also show that the nanoparticulate amorphous cyclosporine formulation is more rapidly absorbed that the conventional NEORAL® formulation. As seen in Table 2, when the dogs were administered nanoparticulate cyclosporine the peak plasma concentrations were all reached in approximately 1 hour or less. When given NEORAL®, peak plasma levels were reached in approximately 1.5 hours for 5 of the six dogs and in approximately 2 hours for dog no. 408/f/1 (Table 3).

These results demonstrate the superior consistency of bioavailability and more rapid absorption among different subjects of the inventive compositions over a conventional cyclosporine formulation, such as NEORAL®.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents. The following examples further illustrate the invention and are not to be construed as limiting of the specification and claims in any way.

We claim:
1. A nanoparticulate composition comprising:
   (a) amorphous cyclosporin particles; and
   (b) at least one non-crosslinked surface stabilizer adsorbed on the surface of the cyclosporin particles,
   wherein: (i) the cyclosporin particles have an effective average particle size of less than about 2000 nm, and (ii) the cyclosporin and at least one surface stabilizer are present in a ratio of about 10:1 to about 1.5:1 (w/w), cyclosporin to surface stabilizer and (iii) the nanoparticulate composition does no contain an alcohol solubilizing agent and (iv) wherein the nanoparticulate composition does not contain solvent residues resulting from solvent extraction, solvent precipitation, or solvent-mediated hydrosol formation.

2. The composition of claim 1, wherein the effective average particle size of the nanoparticulate composition is less than about 1500 nm.

3. The composition of claim 1, wherein said composition is a solid dose formulation.

4. The solid dose composition of claim 3, wherein said composition has a drug to surface stabilizer ratio of at least 2:1.

5. The composition of claim 1, wherein said composition is an liquid dispersion formulation.

6. The liquid dispersion of claim 5, wherein the solid content of said dispersion is about 40% to about 5% (w/w).

7. The composition of claim 5, wherein said composition is an injectable formulation.

8. The composition of claim 1, wherein the surface stabilizer is selected from the group consisting of cetyl pyridinium chloride, gelatin, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, sodium dodecylsulfate, carboxymethylcellulose calcium, hydroxypropyl celluloses, hydroxypropyl methylcellulose, hydroxypropylcellulose, carboxymethylcellulose sodium, methylcellulose, hydroxyethylcellulose, hydroxypropylmethyl-cellulose phthalate, noncrystalline cellulose, polyvinyl alcohol, polyvinylpyrrolidone, 4-(1,1,3,3-tetramethylbutyl)-phenol polymer with ethylene oxide and formaldehyde, poloxamers, poloxamines, dimyristoyl phophatidyl glycerol, dioctylsulfosuccinate, dialkylesters of sodium sulfosuccinic acid, sodium lauryl sulfate, an alkyl aryl polyether sulfonate, a mixture of sucrose stearate and sucrose distearate, p-isononylphenoxypoly-(glycidol), and triblock copolymers of the structure -(-PEO)--(-PBO-)--(-PEO-)-.

9. The composition of claim 8, wherein the surface stabilizer is selected from the group consisting of: (1) a block copolymer of ethylene oxide and propylene oxide, (2) a triblock copolymer of the structure -(-PEO)--(-PBO-)--(-PEO- and having a molecular weight of about 5000, (3) 4-(1,1,3,3-tetramethylbutyl)-phenol polymer with ethylene oxide and formaldehyde, (4) hydroxypropyl cellulose, and (5) sodium lauryl sulfate.

10. A pharmaceutical composition comprising the amorphous cyclosporine composition of claim 1 and a pharmaceutically acceptable excipient.

11. A nanoparticulate composition comprising:
 (a) a mixture of amorphous and crystalline cyclosporin particles; and
 (b) at least one non-crosslinked surface stabilizer absorbed on the surface of the cyclosporin particles,
 wherein: (i) the cyclosporin particles have an effective average particle size of less than about 2000 nm, and (ii) the cyclosporin and at least one surface stabilizer are present in a ratio of about 10:1 to about 1.5:1 (w/w), cyclosporin to surface stabilizer and (iii) the nanoparticulate composition does no contain an alcohol solubilizing agent and (iv) wherein the nanoparticulate composition does not contain solvent residues resulting from solvent extraction, solvent precipitation, or solvent-mediated hydrosol formation.

12. The composition of claim 11, wherein the effective average particle size of the nanoparticulate composition is less than about 1500 nm.

13. The composition of claim 11, wherein said composition is a solid dose formulation.

14. The solid dose composition of claim 13, wherein said composition has a drug to surface stabilizer ratio of at least 2:1.

15. The composition of claim 11, wherein said composition is an liquid dispersion formulation.

16. The liquid dispersion of claim 15, wherein the solid content of said dispersion is about 40% to about 5% (w/w).

17. The composition of claim 11, wherein said composition is an injectable formulation.

18. The composition of claim 11, wherein the surface stabilizer is selected from the group consisting of cetyl pyridinium chloride, gelatin, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, sodium dodecylsulfate, carboxymethylcellulose calcium, hydroxypropyl celluloses, hydroxypropyl methylcellulose, hydroxypropylcellulose, carboxymethylcellulose sodium, methylcellulose, hydroxyethylcellulose, hydroxypropylmethyl-cellulose phthalate, noncrystalline cellulose, polyvinyl alcohol, polyvinylpyrrolidone, 4-(1,1,3,3-tetramethylbutyl)-phenol polymer with ethylene oxide and formaldehyde, poloxamers, poloxamines, dimyristoyl phophatidyl glycerol, dioctylsulfosuccinate, dialkylesters of sodium sulfosuccinic acid, sodium lauryl sulfate, an alkyl aryl polyether sulfonate, a mixture of sucrose stearate and sucrose distearate, p-isononylphenoxypoly-(glycidol), and triblock copolymers of the structure -(-PEO)--(-PBO-)--(-PEO-)-.

19. The composition of claim 18, wherein the surface stabilizer is selected from the group consisting of: (1) a block copolymer of ethylene oxide and propylene oxide, (2) a triblock copolymer of the structure -(-PEO)--(-PBO-)--(-PEO-)- and having a molecular weight of about 5000, (3) 4-(1,1,3,3-tetramethylbutyl)-phenol polymer with ethylene oxide and formaldehyde, (4) hydroxypropyl cellulose, and (5) sodium lauryl sulfate.

20. A pharmaceutical composition comprising the amorphous cyclosporine composition of claim 11 and a pharmaceutically acceptable excipient.

21. A method of making a nanoparticulate composition comprising:
 (a) amorphous cyclosporin particles; and
 (b) at least one non-crosslinked surface stabilizer absorbed on the surface of the cyclosporin particles,
 wherein: (i) the cyclosporin particles have an effective average particle size of less than about 1000 nm, and (ii) the cyclosporin and the at least one surface stabilizer are present in a ratio of about 10:1 to about 1.5:1 (w/w), cyclosporin to surface stabilizer,
 said method comprising contacting cyclosporin with at least one non-crosslinked surface stabilizer for a time and under conditions sufficient to provide a nanoparticulate amorphous cyclosporin composition in which the cyclosporin particles have an average effective particle size of less than about 2000 nm and the composition has a drug to surface stabilizer ratio of about 10:1 to about 1.5:1 (w/w), cyclosporin to surface stabilizer and (iii) the nanoparticulate composition does no contain an alcohol solubilizing agent and (iv) wherein the nanoparticulate composition does not contain solvent residues resulting from solvent extraction, solvent precipitation, or solvent-mediated hydrosol formation.

22. The method of claim 21, wherein the effective average particle size of the nanoparticulate composition is less than about 1500 nm.

23. The method of claim 21, wherein said composition is obtained by milling.

24. The method of claim 23, wherein said milling is high energy milling.

25. The composition of claim 1, wherein the effective average particle size of the nanoparticulate composition is less than about 1000 nm.

26. The composition of claim 1, wherein the effective average particle size of the nanoparticulate composition is less than about 800 nm.

27. The composition of claim 1, wherein the effective average particle size of the nanoparticulate composition is less than about 700 nm.

28. The composition of claim 1, wherein the effective average particle size of the nanoparticulate composition is less than about 600 nm.

29. The composition of claim 1, wherein the effective average particle size of the nanoparticulate composition is less than about 500 nm.

30. The composition of claim 1, wherein the effective average particle size of the nanoparticulate composition is less than about 400 nm.

31. The composition of claim 1, wherein the effective average particle size of the nanoparticulate composition is less than about 300 nm.

32. The composition of claim 1, wherein the effective average particle size of the nanoparticulate composition is less than about 200 nm.

33. The composition of claim 1, wherein the effective average particle size of the nanoparticulate composition is less than about 100 nm.

34. The composition of claim 1, wherein the effective average particle size of the nanoparticulate composition is less than about 50 nm.

35. The composition of claim 11, wherein the effective average particle size of the nanoparticulate composition is less than about 1000 nm.

36. The composition of claim 11, wherein the effective average particle size of the nanoparticulate composition is less than about 800 nm.

37. The composition of claim 11, wherein the effective average particle size of the nanoparticulate composition is less than about 700 nm.

38. The composition of claim 11, wherein the effective average particle size of the nanoparticulate composition is less than about 600 nm.

39. The composition of claim 11, wherein the effective average particle size of the nanoparticulate composition is less than about 500 nm.

40. The composition of claim 11, wherein the effective average particle size of the nanoparticulate composition is less than about 400 nm.

41. The composition of claim 11, wherein the effective average particle size of the nanoparticulate composition is less than about 300 nm.

42. The composition of claim 11, wherein the effective average particle size of the nanoparticulate composition is less than about 200 nm.

43. The composition of claim 11, wherein the effective average particle size of the nanoparticulate composition is less than about 100 nm.

44. The composition of claim 11, wherein the effective average particle size of the nanoparticulate composition is less than about 50 nm.

45. The method of claim 21, wherein the effective average particle size of the nanoparticulate composition is less than about 1000 nm.

46. The method of claim 21, wherein the effective average particle size of the nanoparticulate composition is less than about 800 nm.

47. The method of claim 21, wherein the effective average particle size of the nanoparticulate composition is less than about 700 nm.

48. The method of claim 21, wherein the effective average particle size of the nanoparticulate composition is less than about 600 nm.

49. The method of claim 21, wherein the effective average particle size of the nanoparticulate composition is less than about 500 nm.

50. The method of claim 21, wherein the effective average particle size of the nanoparticulate composition is less than about 400 nm.

51. The method of claim 21, wherein the effective average particle size of the nanoparticulate composition is less than about 300 nm.

52. The method of claim 21, wherein the effective average particle size of the nanoparticulate composition is less than about 200 nm.

53. The method of claim 21, wherein the effective average particle size of the nanoparticulate composition is less than about 100 nm.

54. The method of claim 21, wherein the effective average particle size of the nanoparticulate composition is less than about 50 nm.

55. The composition of claim 1, comprising as at least one surface stabilizer dioctylsulfosuccinate.

56. The composition of claim 1, comprising as surface stabilizers dioctylsulfosuccinate and polyvinylpyrrolidone.

57. The composition of claim 1, comprising as surface stabilizers dioctylsulfosuccinate and HPC-SL.

58. The composition of claim 1, wherein the surface stabilizer is selected from the group consisting of casein, phosphatides, dextran, glycerol, gum acacia, cholesterol, tragacanth, stearic acid, colloidal silicon dioxide, phosphates, magnesium aluminum silicate, and triethanolamine.

59. The composition of claim 11, wherein the surface stabilizer is selected from the group consisting of casein, phosphatides, dextran, glycerol, gum acacia, cholesterol, tragacanth, stearic acid, colloidal silicon dioxide, phosphates, magnesium aluminum silicate, and triethanolamine.

* * * * *